(12) United States Patent
Ichikawa (10) Patent No.: US 7,641,340 B2
(45) Date of Patent: Jan. 5, 2010

(54) FUNDUS CAMERA

(75) Inventor: Naoki Ichikawa, Okazaki (JP)

(73) Assignee: Nidek Co., Ltd., Gamagori (JP)

( * ) Notice: Subject to any disclaimer, the term of this patent is extended or adjusted under 35 U.S.C. 154(b) by 135 days.

(21) Appl. No.: 12/073,007

(22) Filed: Feb. 28, 2008

(65) Prior Publication Data

US 2008/0212028 A1    Sep. 4, 2008

(30) Foreign Application Priority Data

Mar. 1, 2007    (JP) ............................. 2007-052100

(51) Int. Cl.
*A61B 3/14* (2006.01)
(52) U.S. Cl. .................. 351/208; 351/206; 351/210
(58) Field of Classification Search ................. 351/205, 351/206, 208, 210, 211, 212, 221, 247
See application file for complete search history.

(56) References Cited

U.S. PATENT DOCUMENTS

| 4,257,688 | A |  | 3/1981 | Matsumura |  |
| 5,463,430 | A |  | 10/1995 | Isogai et al. |  |
| 7,275,824 | B2 | * | 10/2007 | Hoshino | ..................... 351/206 |
| 7,331,670 | B2 |  | 2/2008 | Ichikawa |  |
| 7,354,153 | B2 | * | 4/2008 | Tawada et al. | .............. 351/206 |
| 2003/0076477 | A1 |  | 4/2003 | Matsumoto |  |
| 2005/0225722 | A1 |  | 10/2005 | Tawada et al. |  |
| 2006/0114412 | A1 |  | 6/2006 | Tawada |  |
| 2007/0013867 | A1 |  | 1/2007 | Ichikawa |  |

FOREIGN PATENT DOCUMENTS

| EP | 1 535 566 A1 | 6/2005 |
| JP | A-63-194634 | 8/1988 |
| JP | A-3-15438 | 1/1991 |
| JP | A-6-46999 | 2/1994 |
| JP | A-2005-160550 | 6/2005 |
| JP | A-2007-202724 | 8/2007 |

* cited by examiner

*Primary Examiner*—Huy K Mai
(74) *Attorney, Agent, or Firm*—Oliff & Berridge, PLC (57) ABSTRACT

A fundus camera of which the operability in alignment when photographing a fundus is enhanced includes a photographing optical system having a photographing optical axis which photographs the fundus, a fundus observation optical system picking up a fundus observation image, an anterior-segment observation optical system picking up an anterior-segment observation image, a photographing unit housing the optical systems, a moving mechanism moving the unit for alignment of the axis, a display unit, and a controller controlling the display unit and making display switching between the images on a screen of the display unit, wherein the controller includes a program for forming and displaying a reticle mark both in displaying the fundus observation image and in displaying the anterior-segment observation image while forming and displaying an alignment mark of which a relative distance from the reticle mark varies with an alignment deviation amount of the axis with respect to an eye.

7 Claims, 4 Drawing Sheets

FUNDUS CAMERA

BACKGROUND OF THE INVENTION

1. Field of the Invention

The present invention relates to a fundus camera which photographs a fundus of an examinee's eye.

2. Description of Related Art

There is known a fundus camera which is capable of making display switching between an observation image of an anterior segment of an examinee's eye and an observation image of a fundus of the eye on a monitor (a display). In such an apparatus, at the time of displaying the anterior-segment observation image, alignment of the apparatus with respect to the eye is performed based on a corneal reflection image of a first alignment target which is picked up by an optical system for picking up the anterior-segment observation image and a reticle mark for the first alignment target which is electrically formed, meanwhile at the time of displaying the fundus observation image, alignment of the apparatus with respect to the eye is performed based on a corneal reflection image of a second alignment target (what is called, a working dot) which is picked up by an optical system for picking up the fundus observation image and a reticle mark for the second alignment target which is electrically formed (see U.S. Pat. No. 7,331,670 corresponding to Japanese Patent Application Unexamined Publication No. 2005-160550).

However, since the alignment at the time of displaying the anterior-segment observation image is differently performed from the alignment at the time of displaying the fundus observation image, it is difficult for an inexperienced examiner to operate such an apparatus, and efficient photographing cannot be performed.

SUMMARY OF THE INVENTION

An object of the invention is to overcome the problems described above and to provide a fundus camera such that the operability of the fundus camera in performing alignment at the time of photographing a fundus is enhanced.

To achieve the objects and in accordance with the purpose of the present invention, a fundus camera includes a photographing optical system having a photographing optical axis, which photographs a fundus of an examinee's eye, a fundus observation optical system having a first image-pickup element which picks up an observation image of the fundus of the eye, an anterior-segment observation optical system having a second image-pickup element which picks up an observation image of an anterior segment of the eye, a photographing unit which houses the photographing optical system, the fundus observation optical system and the anterior-segment observation optical system, a moving mechanism which moves the photographing unit in order to perform alignment of the photographing optical axis so as to have a predetermined positional relationship with the eye, a display unit, and a controller which controls the display unit, and makes display switching between the fundus observation image and the anterior-segment observation image on a screen of the display unit, wherein the controller includes a program for electrically forming and displaying a reticle mark that defines an alignment reference in a predetermined position on the screen both at the time of displaying the fundus observation image and at the time of displaying the anterior-segment observation image while electrically forming and displaying on the screen an alignment mark of which a relative distance from the reticle mark varies in accordance with an alignment deviation amount of the photographing optical axis with respect to the eye which is obtained based on an output signal from the second image-pickup element.

In another aspect of the present invention, a fundus camera includes a photographing optical system having a photographing optical axis, which photographs a fundus of an examinee's eye, a fundus observation optical system having a first image-pickup element which picks up an observation image of the fundus of the eye, an anterior-segment observation optical system having a second image-pickup element which picks up an observation image of an anterior segment of the eye, a photographing unit which houses the photographing optical system, the fundus observation optical system and the anterior-segment observation optical system, a moving mechanism which moves the photographing unit in order to perform alignment of the photographing optical axis so as to have a predetermined positional relationship with the eye, a display unit, and a controller which controls the display unit, and makes display switching between the fundus observation image and the anterior-segment observation image on a screen of the display unit, wherein the controller includes a program for electrically forming and displaying a reticle mark that defines an alignment reference in a predetermined position on the screen at least one of at the time of displaying the fundus observation image and at the time of displaying the anterior-segment observation image while electrically forming and displaying on the screen an alignment mark of which a relative distance from the reticle mark varies in accordance with an alignment deviation amount of the photographing optical axis with respect to the eye which is obtained based on an output signal from the second image-pickup element, and the program is arranged to form and display the alignment mark so that the proportion of change in the relative distance from the reticle mark with respect to the proportion of change in the obtained alignment deviation amount where the obtained alignment deviation amount is large becomes smaller than the proportion of change in the relative distance from the reticle mark with respect to the proportion of change in the obtained alignment deviation amount where the alignment deviation amount is small.

Additional objects and advantages of the invention are set forth in the description which follows, are obvious from the description, or may be learned by practicing the invention. The objects and advantages of the invention may be realized and attained by the fundus camera in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
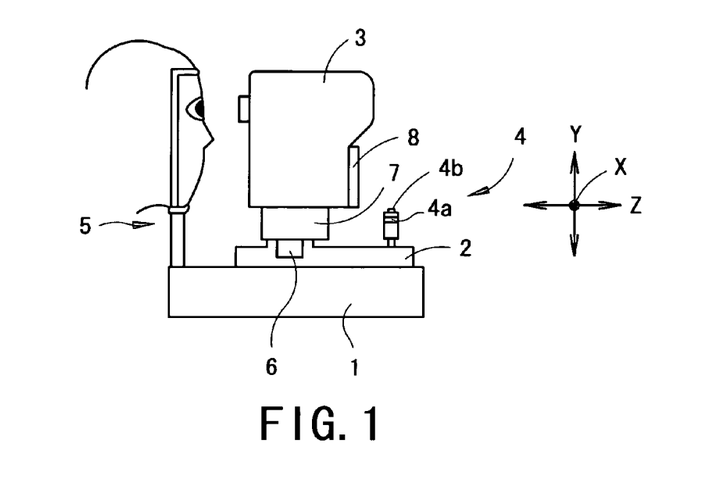
FIG. 1 is a view showing a schematic configuration of a fundus camera according to a preferred embodiment of the present invention.

A detailed description of a fundus camera according to preferred embodiments of the present invention is provided below with reference to the accompanying drawings. FIG. 1 is a view showing a schematic configuration of a fundus camera according to a preferred embodiment of the present invention.

The fundus camera includes a base 1, a mobile base 2 movable in a right/left direction (hereinafter referred to as an "X-direction") and a back/forth direction (hereinafter referred to as a "Z-direction") with reference to the base 1 through tilting operation of a joystick 4, a photographing unit 3 movable in the right/left direction, an up/down direction (hereinafter referred to as a "Y-direction"), and the back/forth direction with reference to the mobile base 2 under control of a controller 80 to be described later, and a face support unit 5 fixedly provided on the base 1 for supporting a face (a head) of an examinee. Moving units 6 and 7 include a Y table movable in the Y-direction, a Z table movable in the Z-direction which is placed on the Y table, and an X table movable in the X-direction which is placed on the Z table, and the photographing unit 3 is placed on the X table. The moving unit 7 moves the X and Z tables respectively by a motor and other moving mechanisms so as to move the photographing unit 3 in the X-direction and/or the Z-direction. The moving unit 6 moves the Y table by a motor and other moving mechanisms so as to move the photographing unit 3 in the Y-direction. Besides, for moving mechanisms as the moving units 6 and 7, a known mechanism may be used. In addition, the photographing unit 3 is moved in the Y-direction also by driving of the moving unit 6 through rotational operation of a rotating knob 4a of the joystick 4. A monitor (a display) 8 which displays images including an observation image of an anterior segment of an examinee's eye, an observation image of a fundus of the eye, and a photographing image of the fundus is provided on the examiner's side of the photographing unit 3.

Figure 2:
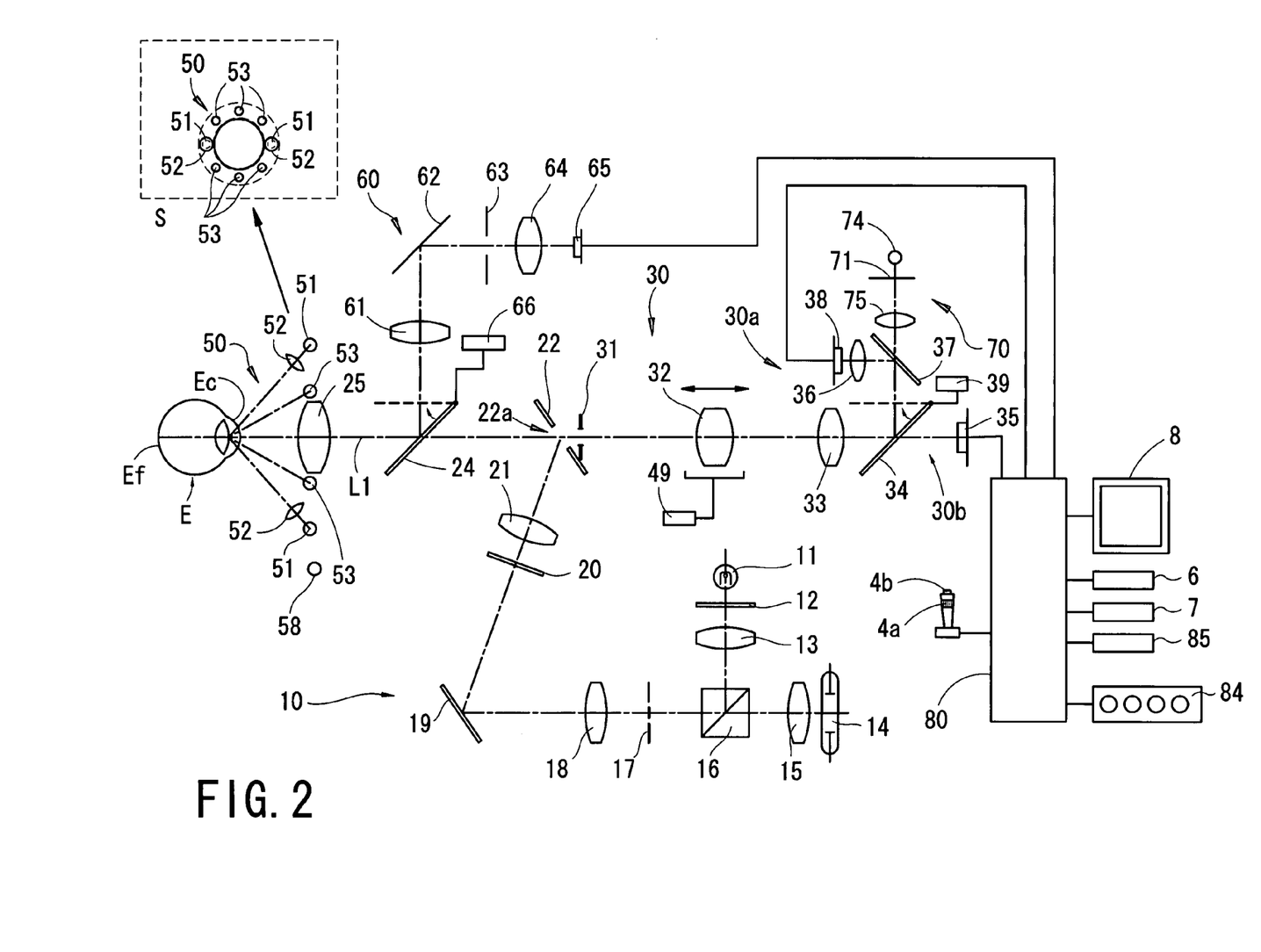
FIG. 2 is a view showing a schematic configuration of an optical system and a control system of the fundus camera.

FIG. 2 is a view showing a schematic configuration of an optical system and a control system housed in the photographing unit 3. The optical system includes an illumination optical system 10, a fundus observation/photographing optical system 30, an alignment target projection optical system 50, an anterior-segment observation optical system 60 and a fixation target presenting optical system 70.

<Illumination Optical System 10>

The illumination optical system 10 includes an illumination optical system for fundus observation and an illumination optical system for photographing. Illumination light emitted from an illumination light source 11 for fundus observation such as a halogen light is made into infrared illumination light by an infrared transmission filter 12 which transmits infrared light with a wavelength of less than about 900 nm, and is reflected by a dichroic mirror 16 via a condenser lens 13. The dichroic mirror 16 has a wavelength-selecting property of reflecting infrared light and transmitting visible light. The infrared illumination light reflected by the dichroic mirror 16 passes through a ring slit plate 17, a relay lens 18, a total reflection mirror 19, a black dot plate 20 having a black dot at its center and a relay lens 21, and is reflected by an apertured mirror 22 and is projected onto a fundus Ef of an examinee's eye E via an objective lens 25. Besides, an infrared light source such as an infrared light-emitting diode may be used instead of the light source 11 such as the halogen light and the infrared transmission filter 12.

Visible illumination light emitted from a visible illumination light source 14 for photographing such as a flash light passes through a condenser lens 15 and is transmitted through the dichroic mirror 16 and is projected onto the fundus Ef via the ring slit plate 17 to the objective lens 25.

<Fundus Observation/Photographing Optical System 30>

The fundus observation/photographing optical system 30 includes a fundus observation optical system 30a and a photographing optical system 30b. The infrared light and the visible light reflected from the fundus Ef pass through the objective lens 25, an aperture 22a in the apertured mirror 22, a photographing diaphragm 31 placed in the vicinity of the aperture 22a and a focusing lens 32 and enter an image forming lens 33. The photographing diaphragm 31 is placed in a position substantially conjugate with a pupil of the eye E with reference to the objective lens 25. The focusing lens 32 is placed so as to be movable by a moving unit 49 consisting of a moving mechanism such as a motor in a direction of an optical axis L1 of the fundus observation/photographing optical system 30 (the objective lens 25). A movable total reflection mirror 34 is placed so as to be insertable into/removable from an optical path of the fundus observation/photographing optical system 30 by an inserting/removing unit 39 consisting of an inserting/removing mechanism such as a motor, and is removed from the optical path at the time of photographing. When the mirror 34 is removed from the optical path, the visible reflection light is photo-received on a CCD camera (an image-pickup element) 35 for photographing having sensitivity to a visible range and forms an image of the fundus Ef (a fundus photographing image). Meanwhile when the mirror 34 is inserted into the optical path, the infrared reflection light reflected by the mirror 34 is reflected by a dichroic mirror 37, is photo-received on a CCD camera (an image-pickup element) 38 for fundus observation having sensitivity to an infrared range via a relay lens 36 and forms an image of the fundus Ef (a fundus observation image). The dichroic mirror 37 has a wavelength-selecting property of reflecting infrared light and transmitting visible light.

A movable dichroic mirror 24 that defines an optical path dividing member is placed so as to be insertable into/removable from an optical path between the objective lens 25 and the apertured mirror 22 (the photographing diaphragm 31) by an inserting/removing unit 66 consisting of an inserting/removing mechanism such as a motor, and is removed from the optical path at the time of photographing. The dichroic mirror 24 has a wavelength-selecting property of reflecting infrared light with a wavelength of about 900 nm or more from an infrared illumination light source 58 for anterior-segment observation and the alignment target projection optical system 50 to be described later, and transmitting the infrared light with the wavelength of less than about 900 nm from the illumination optical system for fundus observation.

<Alignment Target Projection Optical System 50>

As shown in a figure S enclosed with dashed lines in FIG. 2, the alignment target projection optical system 50 includes two first projection optical systems in a pair which have optical axes placed so as to be laterally symmetrical with respect to the optical axis L1, and six second projection optical systems in pairs which have optical axes placed so as to be laterally symmetrical with respect to the optical axis L1. Each of the two first projection optical systems includes an infrared light source 51 such as an infrared light-emitting diode which emits the infrared light with the wavelength of about 900 nm or more and a collimating lens 52 and projects infrared target light at an infinite distance (projects an alignment target at an infinite distance) onto an anterior segment (a cornea Ec) of the eye E with substantially parallel light. Meanwhile each of the six second projection optical systems includes an infrared light source 53 such as an infrared light-emitting diode which emits the infrared light with the wavelength of about 900 nm or more, and projects infrared target light at a finite distance (projects an alignment target at a finite distance) onto the anterior segment (the cornea Ec) of the eye E with divergent light. Besides, in the preferred embodiment of the present invention, as shown in the figure S enclosed with the dashed lines in FIG. 2, the first projection optical systems and the second projection optical systems are placed at intervals of 45° each other on a concentric circle having the optical axis L1 as its center (e.g., a concentric circle of 3-mm radius).

<Anterior-Segment Observation Optical System 60>

Infrared illumination light emitted from the infrared illumination light source 58 for anterior-segment observation such as an infrared light-emitting diode which emits the infrared light with the wavelength of about 900 nm or more is reflected by the anterior segment of the eye E and the dichroic mirror 24 inserted into the optical path, is photo-received on a CCD camera (an image-pickup element) 65 for anterior-segment observation having sensitivity to an infrared range via a field lens 61, a total reflection mirror 62, a diaphragm 63 and a relay lens 64, and forms an image of the anterior segment of the eye E (an anterior-segment observation image). The CCD camera 65 doubles as image-pickup means for alignment target image detection (i.e., the anterior-segment observation optical system 60 doubles as an alignment target image detection optical system), and picks up the anterior-segment image formed by the light source 58 and images of the alignment targets formed by the alignment target projection optical system 50.

<Fixation Target Presenting Optical System 70>

Red fixation target light emitted from a fixation target light source (a fixation lamp) 74 such as a red light-emitting diode passes through an aperture in a shielding plate 71 and a relay lens 75 and is transmitted through the dichroic mirror 37. The red fixation target light transmitted through the dichroic mirror 37 is reflected by the dichroic mirror 34 inserted into the optical path, passes through the image forming lens 33 to the objective lens 25, and is projected onto the fundus Ef (i.e., a fixation target is projected thereonto).

Figure 3A:
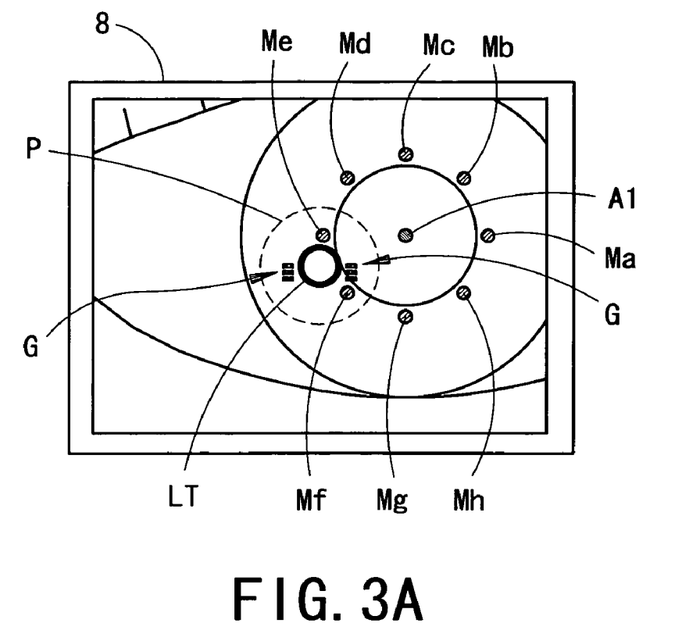
FIGS. 3A and 3B are views showing examples in displaying an observation image of an anterior segment of an examinee's eye.

Image signals outputted from the CCD cameras 65, 38 and 35 are inputted to the controller 80. The controller 80 detects the alignment target images based on the image signal from the CCD camera 65 and obtains an alignment deviation amount $\Delta d$ of the optical axis L1 (the photographing unit 3) with respect to the eye E in the X- and Y-directions. In addition, the controller 80 is connected to the monitor 8 and performs a display control of the monitor 8. For example, both at the time of displaying the anterior-segment observation image by the CCD camera 65 (see FIGS. 3A and 3B) and at the time of displaying the fundus observation image by the CCD camera 38 (see FIGS. 4A and 4B), the controller 80 controls to electrically form and display a reticle mark LT that defines an alignment reference in a predetermined position on a screen of the monitor 8 while controlling to electrically form and display on the screen of the monitor 8 an alignment mark A1 of which a relative distance $\Delta H$ from the reticle mark LT varies in accordance with the alignment deviation amount $\Delta d$ obtained based on the image signal from the CCD camera 65. The controller 80 is connected with the moving units 6, 7 and 49, the inserting/removing units 39 and 66, the rotation knob 4a, a photographing switch 4b, a switch unit 84 including various switches, a memory 85, the light sources, and other constituent elements (in FIG. 2, a part of connection lines are not shown.)

Operation of the fundus camera having the above-described configuration will be described hereinafter. First, the face of the examinee is supported by the face support unit 5. In the initial stage, the dichroic mirror 24 has been already inserted into the optical path, and the anterior-segment observation image picked up by the CCD camera 65 is displayed on the monitor 8. The controller 80 controls to electrically form and display in the center of the screen of the monitor 8 the reticle mark LT and a circular mark P indicating the minimum pupil diameter of photographing. The photographing unit 3 is moved in the X-direction and/or the Y-direction so that the anterior-segment observation image is placed in the center of the screen of the monitor 8. In addition, the photographing unit 3 is moved in the Z-direction so that the anterior-segment observation image is brought into focus. When the anterior-segment observation image comes to be placed in the vicinity of the center of the screen of the monitor 8, eight alignment target images Ma to Mh formed by the alignment target projection optical system 50 come to be displayed (see FIG. 3A).

When the alignment target images Ma to Mh are picked up by the CCD camera 65, the controller 80 obtains the alignment deviation amount $\Delta d$ in the X- and Y-directions based on the image signal from the CCD camera 65. In the preferred embodiment of the present invention, the controller 80 detects a center position of the alignment target images Ma to Mh in the X- and Y-directions as a substantial corneal center, and calculates a difference (a deviation amount) between the center position and an alignment reference position in the X- and Y-directions previously set in the CCD camera 65 (e.g., an intersection point of an image-pickup surface of the CCD camera 65 and the optical axis L1).

Figure 6:
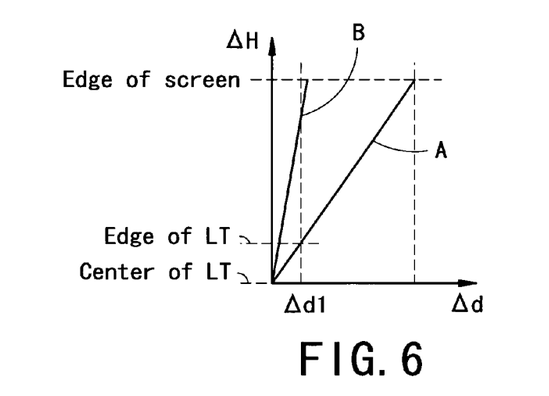
FIG. 6 is a view showing a relationship between an alignment deviation amount and the relative distance of the alignment mark from the reticle mark.

When the center position of the alignment target images Ma to Mh is obtained, the controller 80 controls to electrically form and display the alignment mark A1 in a position on the monitor 8 which corresponds to the center position. In addition, the controller 80 controls display of the alignment mark A1 so that the relative distance $\Delta H$ from the reticle mark LT displayed on the monitor 8 varies in accordance with the alignment deviation amount $\Delta d$ obtained based on the image signal from the CCD camera 65. FIG. 6 is a view showing a relationship between the alignment deviation amount $\Delta d$ and the relative distance $\Delta H$ of the alignment mark A1 from the reticle mark LT. A line A in FIG. 6 indicates a relationship between the alignment deviation amount $\Delta d$ and the relative distance $\Delta H$ at the time of displaying the anterior-segment observation image, and a line B in FIG. 6 indicates a relationship between the alignment deviation amount $\Delta d$ and the relative distance $\Delta H$ at the time of displaying the fundus observation image. Besides, a program for performing the display control of the monitor 8 based on the relationships is previously stored in the memory 85, and the controller 80 performs the display control of the monitor 8 by using the program.

When the alignment deviation amount $\Delta d$ changes by the movement of the photographing unit 3 with respect to the eye E in the X- and Y-directions, the controller 80 controls to change the relative distance $\Delta H$. That is to say, a display position (a formation position) of the alignment mark A1 with respect to the reticle mark LT varies in accordance with the change in the alignment deviation amount $\Delta d$. Besides, in the preferred embodiment of the present invention, a display shape and a display size of the reticle mark LT and a display position of the alignment mark A1 are set so that the alignment of the optical axis L1 (the photographing unit 3) with respect to the eye E in the X- and Y-directions is completed when the alignment mark A1 is displayed within the reticle mark LT.

Figure 3B:
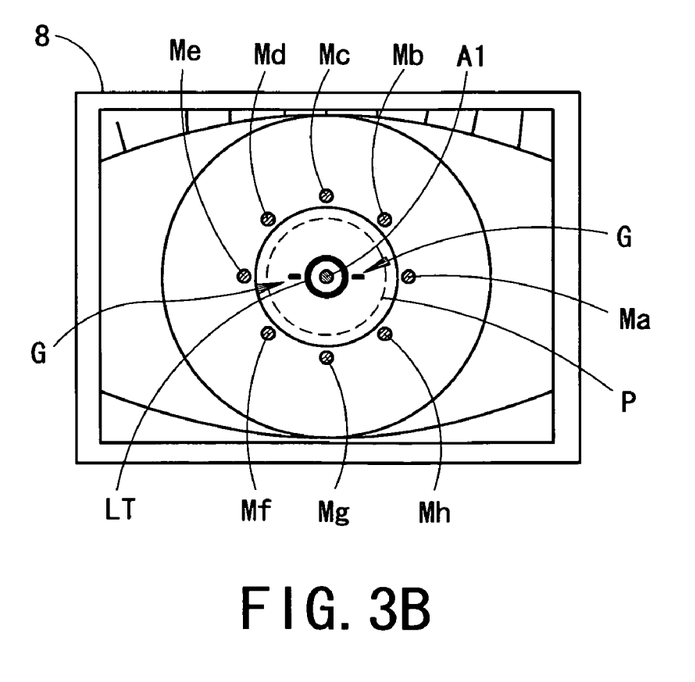

The photographing unit 3 is further moved in the X- and Y-directions so that the alignment mark A1 is displayed within the reticle mark LT (see FIG. 3B). In addition, it is checked whether or not the pupil diameter of the eye E is bigger than the circular mark P indicating the minimum pupil diameter.

In addition, the controller 80 compares an interval between the images of the infinite alignment targets with intervals between the images of the finite alignment targets, and obtains an alignment deviation amount of the photographing unit 3 with respect to the eye E in the Z-direction (see U.S. Pat. No. 5,463,430 corresponding to Japanese Patent Application Unexamined Publication No. Hei06-46999). Then, the controller 80 increases/decreases the number of indicators G based on the alignment deviation amount in the Z-direction which is obtained based on the image signal from the CCD camera 65. Then, the photographing unit 3 is moved in the Z-direction so that only one indicator G is displayed (see FIG. 3B), and alignment of the photographing unit 3 with respect to the eye E in the Z-direction is performed.

The controller 80 judges whether or not the alignment in the X- and Y-directions is performed appropriately by determining whether or not the alignment deviation amount Δd in the X- and Y-directions stays within a predetermined range of alignment completion for a given period of time. In addition, the controller 80 judges whether or not the alignment in the Z-direction is performed appropriately by determining whether or not the alignment deviation amount in the Z-direction stays within a predetermined range of alignment completion for a given period of time.

When the alignment states in the X-, Y- and Z-directions satisfy predetermined conditions for alignment completion, the controller 80 automatically switches the display on the monitor 8 from the anterior-segment observation image to the fundus observation image. Besides, instead of the automatic display switching being performed, a message for manual display switching may be informed (displayed).

At the time of displaying the fundus observation image, the controller 80, similarly to the case of displaying the anterior-segment observation image, controls to electrically form and display the reticle mark LT in a predetermined position on the screen of the monitor 8 while controlling to electrically form and display on the screen of the monitor 8 the alignment mark A1 of which the relative distance ΔH from the reticle mark LT varies in accordance with the alignment deviation amount Δd. That is to say, in the preferred embodiment of the present invention, both in the anterior-segment observation image and in the fundus observation image, between which the display on the monitor 8 is switched, the alignment deviation amounts of the optical axis L1 (the photographing unit 3) with respect to the eye E are displayed in the same manner. To be more specific, the alignment deviation amount is shown by one circle (the reticle mark LT) displayed in a predetermined position and one dot (the alignment mark A1) of which a display position changes. Besides, the reticle mark LT may be displayed in different positions in displaying the anterior-segment observation image and in displaying the fundus observation image.

The controller 80 controls the display position of the alignment mark A1 so that the relative distance ΔH corresponding to the alignment deviation amount Δd (e.g., Δd1) at the time of displaying the fundus observation image differs from that at the time of displaying the anterior-segment observation image. To be more specific, the controller 80 controls the display of the alignment mark A1 so that the relative distance ΔH from the reticle mark LT in accordance with the alignment deviation amount Δd at the time of displaying the fundus observation image becomes longer (e.g., about four or five times) than that at the time of displaying the anterior-segment observation image. That is to say, the controller 80 controls the display of the alignment mark A1 so that a proportion of change in the relative distance ΔH with respect to a proportion of change in the alignment deviation amount ΔH at the time of displaying the fundus observation image becomes larger than that at the time of displaying the anterior-segment observation image.

Figure 4A:
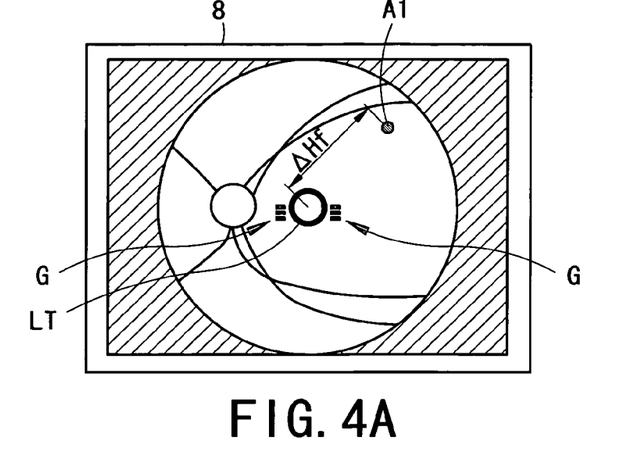
FIGS. 4A and 4B are views showing examples in displaying an observation image of a fundus of the eye.
Figure 4B:
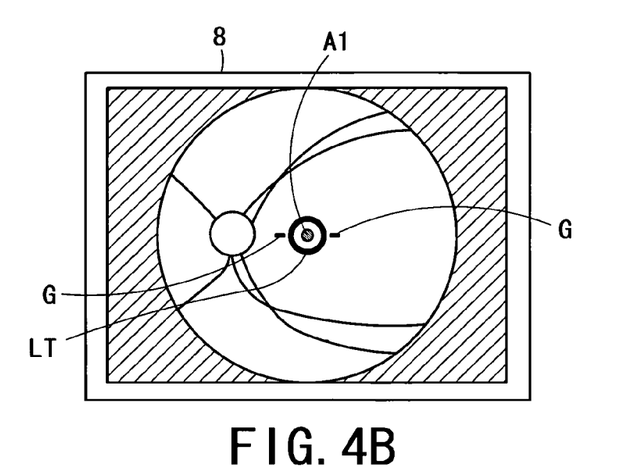
Figure 5:
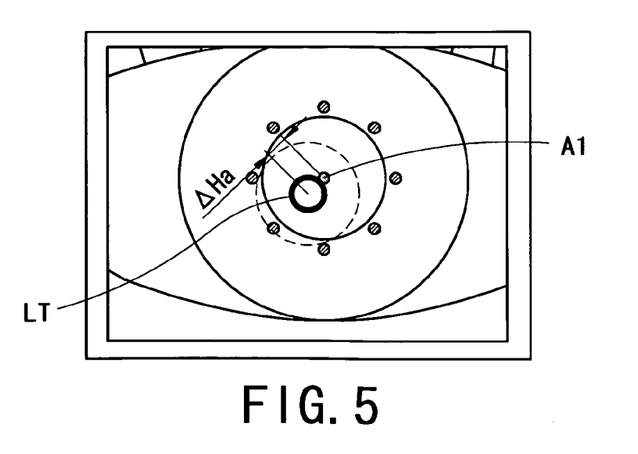
FIG. 5 is a view showing a relative distance of an alignment mark from a reticle mark.

In FIG. 4A, a relative distance ΔHf indicates the relative distance ΔH corresponding to the alignment deviation amount Δd1 at the time of displaying the fundus observation image. In FIG. 5, a relative distance ΔHa indicates the relative distance ΔH corresponding to the alignment deviation amount Δd1 at the time of displaying the anterior-segment observation image.

Besides, the controller 80 deletes the alignment mark A1 from the screen of the monitor 8 if the alignment deviation amount Δd exceeds a predetermined upper limit (e.g., 1.5 mm) at the time of displaying the fundus observation image.

In addition, also in the Z-direction, the controller 80 increases/decreases the number of indicators G based on the alignment deviation amount in the Z-direction similarly to the case of displaying the anterior-segment observation image. In this case, similarly to the case of the alignment in the X- and Y-directions, display of the indicators G (e.g., the number of the indicators G) varying in accordance with the alignment deviation amount in the Z-direction at the time of displaying the fundus observation image may differ from that at the time of displaying the anterior-segment observation image.

The photographing unit 3 is moved in the X- and Y-directions so that the alignment mark A1 is displayed within the reticle mark LT (see FIG. 4B) and the alignment of the optical axis L1 (the photographing unit 3) with respect to the eye E in the X- and Y-directions is performed. In addition, the photographing unit 3 is moved in the Z-direction so that only one indicator G is displayed (see FIG. 4B), and the alignment of the photographing unit 3 with respect to the eye E in the Z-direction is performed. Besides, in a case where the alignment of the optical axis L1 with respect to the eye E deviates widely and the alignment mark A1 is deleted, the display on the monitor 8 is automatically switched from the fundus observation image to the anterior-segment observation image. Also at this time, a message for the manual display switching may be informed (displayed) instead of the automatic display switching being performed.

Next, focusing is performed through operation of a focusing switch in the switch unit 84 while the fundus observation image on the monitor 8 is observed. The controller 80 drives the moving unit 49 and moves the focusing lens 32 based on an input signal by the focusing switch. Then, when a desired portion of the fundus Ef becomes preferably observable, photographing is performed through operation of the switch 4b. The controller 80 drives the inserting/removing unit 39 so as to remove the mirror 34 from the optical path, drives the inserting/removing unit 66 so as to remove the dichroic mirror 24 from the optical path, and lights the light source 14. The fundus photographing image picked up by the CCD camera 35 is stored in the memory 85 and displayed on the monitor 8.

As described above, since the alignment mark A1 of which the relative distance ΔH from the reticle mark LT varies in accordance with the alignment deviation amount Δd is formed and displayed both at the time of displaying the anterior-segment observation image and at the time of displaying the fundus observation image, the alignment at the time of displaying the fundus observation image and the alignment at the time of displaying the anterior-segment observation image can be performed with the same operability, which allows efficient photographing to be performed.

In addition, since the alignment mark A1 is formed and displayed so that the proportion of change in the relative distance ΔH with respect to the proportion of change in the alignment deviation amount Δd at the time of displaying the fundus observation image becomes larger than that at the time of displaying the anterior-segment observation image, rough alignment is easily performed at the time of displaying the anterior-segment observation image and precise alignment is easily performed at the time of displaying the fundus observation image, which allows efficient photographing to be performed.

Figure 7A:
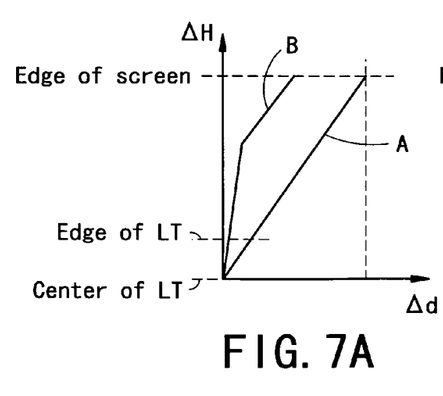
FIGS. 7A and 7B are views showing relationships between the alignment deviation amount and the relative distance of the alignment mark from the reticle mark.
Figure 7B:
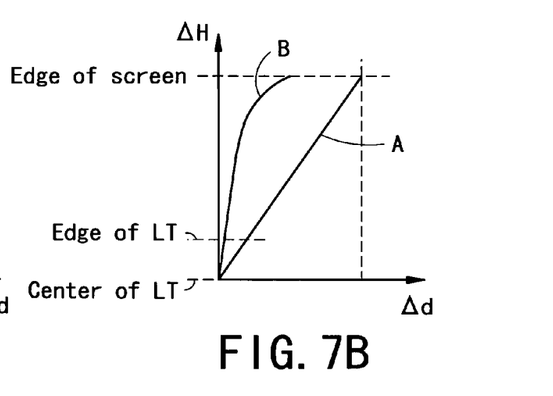

Incidentally, in the above description, the alignment mark A1 is formed and displayed so that the relative distance ΔH varies linearly in accordance with the change in the alignment deviation amount Δd (see FIG. 6). However, it is not limited thereto and the alignment mark A1 may be formed and displayed so that the relative distance ΔH varies nonlinearly in accordance with the change in the alignment deviation amount Δd. That is to say, the controller 80 controls to form and display the alignment mark A1 so that the proportion of change in the relative distance ΔH with respect to the proportion of change in the alignment deviation amount Δd where the alignment deviation amount Δd is large becomes smaller than the proportion of change in the relative distance ΔH with respect to the proportion of change in the alignment deviation amount Δd where the alignment deviation amount Δd is small. For example, as shown in FIGS. 7A and 7B, the alignment mark A1 may be formed and displayed so that the relative distance ΔH varies nonlinearly in accordance with the change in the alignment deviation amount Δd at the time of displaying the fundus observation image. This makes it possible for the relative distance ΔH corresponding to the alignment deviation amount Δd to be displayed larger in a state closer to a correct alignment state at the time of displaying the fundus observation image, whereby precise alignment can be performed with efficiency even by an inexperienced examiner.

Besides, the alignment mark A1 may be formed and displayed so that the relative distance ΔH varies nonlinearly in accordance with the change in the alignment deviation amount Δd at the time of displaying the anterior-segment observation image.

The display switching between the anterior-segment observation image and the fundus observation image includes a case where the anterior-segment observation image is largely displayed where the fundus observation image is synthetically displayed in a small window when the display is switched to a state of the anterior segment observation (a state at the time of displaying the anterior-segment observation image), and a case where the fundus observation image is largely displayed where the anterior-segment observation image is synthetically displayed in a small window when the display is switched to a state of the fundus observation (a state at the time of displaying the fundus observation image).

When the alignment deviation amount Δd exceeds the predetermined upper limit, it is also preferable for the alignment mark A1 to be displayed on the edge of the screen of the monitor 8 instead of being deleted from the screen.

In addition, the reticle mark LT at the time of displaying the fundus observation image may be formed and displayed in a smaller size than the reticle mark LT at the time of displaying the anterior-segment observation image. Accordingly, rough alignment is performed at the time of displaying the anterior-segment observation image and precise alignment is performed at the time of displaying the fundus observation image.

Incidentally, when the proportion of change in the relative distance ΔH with respect to the proportion of change in the alignment deviation amount Δd is larger (e.g., at the time of displaying the fundus observation image), there may be a case where stability of the display position of the alignment mark A1 is not achieved due to involuntary fine movement of the eye E which is fixated when the alignment deviation amount Δd is obtained based on the image signal from the CCD camera 65 which is outputted at a predetermined frame rate and the display of the alignment mark A1 is controlled.

Hence, the controller 80 may be arranged to control the display of the alignment mark A1 based on an average of a plurality of the alignment deviation amounts obtained with time based on the image signals from the CCD camera 65. In this case, emphasis may be placed on the alignment deviation amount which is obtained most recently. By this arrangement, the stability of the display position of the alignment mark A1 is achieved.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera comprising:
    a photographing optical system having a photographing optical axis, which photographs a fundus of an examinee's eye;
    a fundus observation optical system having a first image-pickup element which picks up an observation image of the fundus of the eye;
    an anterior-segment observation optical system having a second image-pickup element which picks up an observation image of an anterior segment of the eye;
    a photographing unit which houses the photographing optical system, the fundus observation optical system and the anterior-segment observation optical system;
    a moving mechanism which moves the photographing unit in order to perform alignment of the photographing optical axis so as to have a predetermined positional relationship with the eye;
    a display unit; and
    a controller which controls the display unit, and makes display switching between the fundus observation image and the anterior-segment observation image on a screen of the display unit, wherein
    the controller includes a program for electrically forming and displaying a reticle mark that defines an alignment reference in a predetermined position on the screen both at the time of displaying the fundus observation image and at the time of displaying the anterior-segment observation image while electrically forming and displaying on the screen an alignment mark of which a relative distance from the reticle mark varies in accordance with an alignment deviation amount of the photographing optical axis with respect to the eye which is obtained based on an output signal from the second image-pickup element.

2. The fundus camera according to claim 1, wherein the program is arranged to form and display the alignment mark so that a proportion of change in the relative distance from the reticle mark with respect to a proportion of change in the obtained alignment deviation amount at the time of displaying the fundus observation image becomes larger than a proportion of change in the relative distance from the reticle mark with respect to a proportion of change in the obtained alignment deviation amount at the time of displaying the anterior-segment observation image.

3. The fundus camera according to claim 2, wherein the program is arranged to form and display the alignment mark so that a proportion of change in the relative distance from the reticle mark with respect to a proportion of change in the obtained alignment deviation amount where the obtained alignment deviation amount is large becomes smaller than a proportion of change in the relative distance from the reticle mark with respect to a proportion of change in the obtained alignment deviation amount where the alignment deviation amount is small.

4. The fundus camera according to claim 1, wherein the program is arranged to form and display the reticle mark at the time of displaying the fundus observation image in a smaller size than the reticle mark at the time of displaying the anterior-segment observation image.

5. The fundus camera according to claim 1, wherein the program is arranged to form and display the alignment mark of which the relative distance from the reticle mark varies in accordance with an average of the alignment deviation amounts obtained with time.

6. A fundus camera comprising:
a photographing optical system having a photographing optical axis, which photographs a fundus of an examinee's eye;
a fundus observation optical system having a first image-pickup element which picks up an observation image of the fundus of the eye;
an anterior-segment observation optical system having a second image-pickup element which picks up an observation image of an anterior segment of the eye;
a photographing unit which houses the photographing optical system, the fundus observation optical system and the anterior-segment observation optical system;
a moving mechanism which moves the photographing unit in order to perform alignment of the photographing optical axis so as to have a predetermined positional relationship with the eye;
a display unit; and
a controller which controls the display unit, and makes display switching between the fundus observation image and the anterior-segment observation image on a screen of the display unit, wherein
the controller includes a program for electrically forming and displaying a reticle mark that defines an alignment reference in a predetermined position on the screen at least one of at the time of displaying the fundus observation image and at the time of displaying the anterior-segment observation image while electrically forming and displaying on the screen an alignment mark of which a relative distance from the reticle mark varies in accordance with an alignment deviation amount of the photographing optical axis with respect to the eye which is obtained based on an output signal from the second image-pickup element, and
the program is arranged to form and display the alignment mark so that a proportion of change in the relative distance from the reticle mark with respect to a proportion of change in the obtained alignment deviation amount where the obtained alignment deviation amount is large becomes smaller than a proportion of change in the relative distance from the reticle mark with respect to a proportion of change in the obtained alignment deviation amount where the alignment deviation amount is small.

7. The fundus camera according to claim 6, wherein the program is arranged to form and display the alignment mark of which the relative distance from the reticle mark varies in accordance with an average of the alignment deviation amounts obtained with time.

* * * * *